United States Patent
Klasovsky et al.

(10) Patent No.: US 8,981,159 B2
(45) Date of Patent: Mar. 17, 2015

(54) CONTINUOUSLY OPERABLE METHOD FOR PRODUCING CARBONYL COMPOUNDS BY MEANS OF A CATALYST CONTAINING A NITROXYL RADICAL

(75) Inventors: Florian Klasovsky, Haltern am See (DE); Thomas Haas, Muenster (DE); Thomas Tacke, Alzenau (DE); Jan Christoph Pfeffer, Hanau (DE); Michael Rimbach, Herne (DE); Michael Volland, Duelmen (DE); Michiel Janssen, The Hague (NL); Roger Sheldon, Hoog-Kappel (NL); Juergen Haberland, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/110,450

(22) PCT Filed: Dec. 6, 2011

(86) PCT No.: PCT/EP2011/071911
§ 371 (c)(1),
(2), (4) Date: Oct. 8, 2013

(87) PCT Pub. No.: WO2012/139666
PCT Pub. Date: Oct. 18, 2012

(65) Prior Publication Data
US 2014/0039223 A1    Feb. 6, 2014

(30) Foreign Application Priority Data

Apr. 12, 2011 (EP) .................... 11162077

(51) Int. Cl.
*C07C 45/59* (2006.01)
*C07D 493/04* (2006.01)
(52) U.S. Cl.
CPC .............. *C07C 45/59* (2013.01); *C07D 493/04* (2013.01)
USPC ........... 568/386; 568/320; 568/322; 568/351; 549/464
(58) Field of Classification Search
CPC ........ C07C 45/59; C07C 45/38; C07C 45/39; C07D 493/04
USPC ................... 568/320, 322, 351, 386; 549/464
See application file for complete search history.

(56) References Cited

U.S. PATENT DOCUMENTS

| | | |
|---|---|---|
| 5,136,103 A | 8/1992 | Fried |
| 5,155,279 A | 10/1992 | Fried |
| 5,155,280 A | 10/1992 | Fried |
| 7,030,279 B1 | 4/2006 | Tanielyan et al. |
| 8,372,595 B2 | 2/2013 | Schaffer et al. |
| 8,378,127 B2 | 2/2013 | Dingerdissen et al. |
| 2010/0261237 A1 | 10/2010 | Verseck et al. |
| 2010/0324257 A1 | 12/2010 | Karau et al. |
| 2011/0171702 A1 | 7/2011 | Reinecke et al. |
| 2011/0251399 A1 | 10/2011 | Dingerdissen et al. |
| 2011/0269977 A1 | 11/2011 | Dingerdissen et al. |
| 2012/0041216 A1 | 2/2012 | Sieber et al. |
| 2013/0052700 A1 | 2/2013 | Poetter et al. |
| 2013/0164797 A1 | 6/2013 | Gielen et al. |
| 2013/0165672 A1 | 6/2013 | Klasovsky et al. |
| 2014/0039223 A1 | 10/2013 | Klasovsky et al. |

FOREIGN PATENT DOCUMENTS

| | | |
|---|---|---|
| EP | 1 674 440 | 6/2006 |
| WO | 2008 148640 | 12/2008 |
| WO | 2010 089213 | 8/2010 |
| WO | 2010 089223 | 8/2010 |
| WO | 2012 031884 | 3/2012 |
| WO | 2012 113475 | 8/2012 |

OTHER PUBLICATIONS

U.S. Appl. No. 14/000,400, filed Aug. 20, 2013, Klaskovsky, et al.
International Search Report Issued Dec. 30, 2011 in PCT/EP11/71911 Filed Dec. 6, 2011.
U.S. Appl. No. 14/357,322, filed May 9, 2014, Markowz, et al.

*Primary Examiner* — Sikarl Witherspoon
(74) *Attorney, Agent, or Firm* — Oblon, McClelland, Maier & Neustadt, L.L.P.

(57) ABSTRACT

The invention relates to a method for the oxidation of a primary or secondary alcohol, preferably to form an aldehyde or ketone, comprising the following steps: a) providing a catalyst composition comprising at least one compound containing a nitroxyl radical, at least one NO source, at least one carbon or mineral acid or an anhydride of a carbon or mineral acid; b) producing a reaction mixture by adding at least one primary or secondary alcohol and a gas comprising oxygen and optionally one or more than one solvent to the catalyst composition from step a) or step e); c) incubating the reaction mixture from step b) at a temperature of between 0 and 100° C. or at the boiling point of the solvent; d) simultaneously with or subsequent to step c): crystallizing the reaction product; and e) recovering the catalyst composition by removing the crystallized reaction product from the reaction mixture obtained in step d).

19 Claims, 1 Drawing Sheet

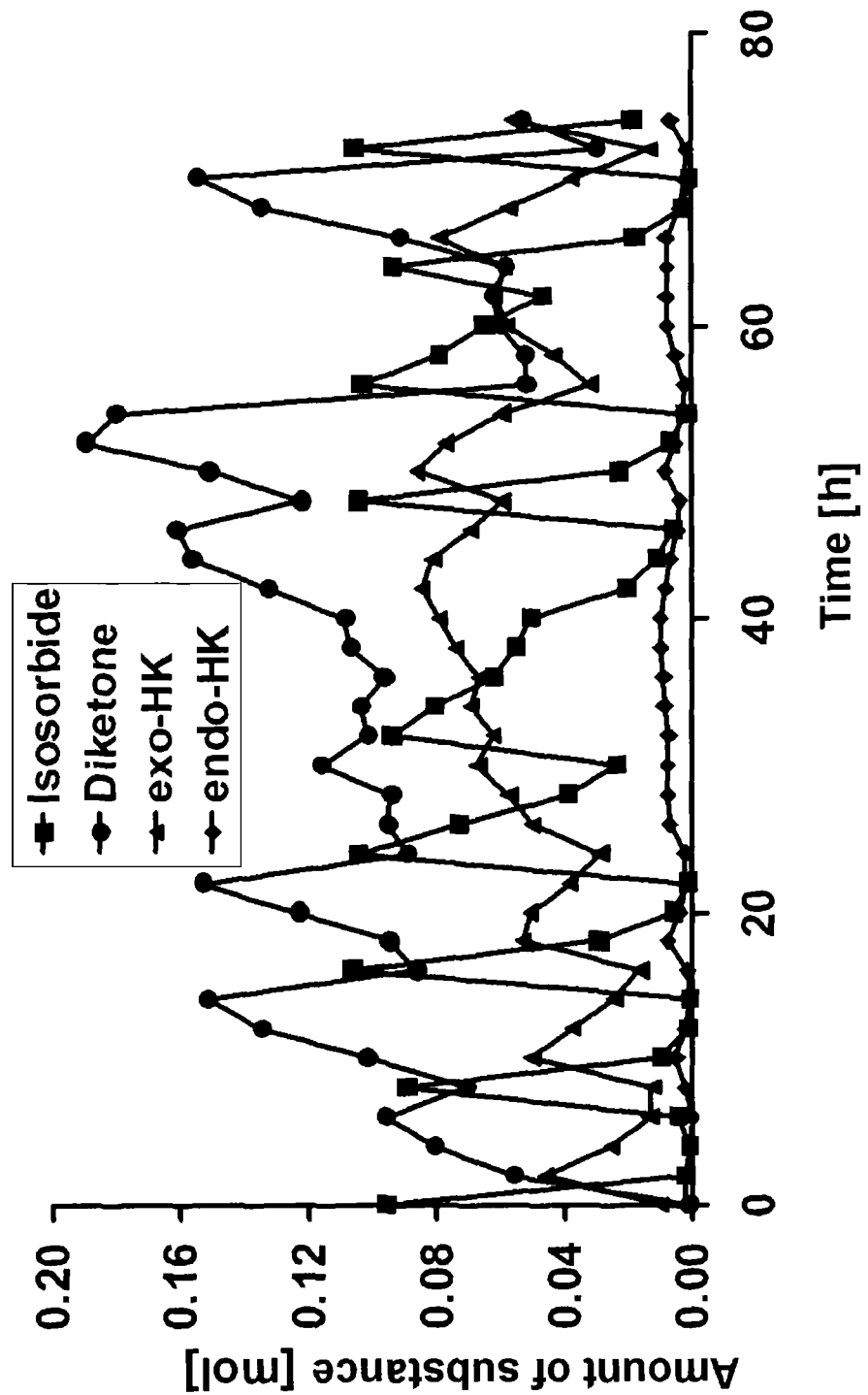

CONTINUOUSLY OPERABLE METHOD FOR PRODUCING CARBONYL COMPOUNDS BY MEANS OF A CATALYST CONTAINING A NITROXYL RADICAL

CROSS REFERENCE TO RELATED APPLICATIONS

The present application is a 35 U.S.C. §371 national stage patent application of International patent application PCT/EP2011/071911, filed on Dec. 6, 2011, published as WO/2012/139666 on Oct. 18, 2012, the text of which is incorporated by reference, and claims the benefit of the filing date of EP application no. 11162077.9, filed on Apr. 12, 2011, the text of which is also incorporated by reference.

The present invention relates to a method for oxidizing a primary or secondary alcohol, preferably to the aldehyde or ketone, by using a nitroxyl radical-containing catalyst composition and the recovery of this catalyst composition.

Carbonyl compounds, comprising two classes of chemical compounds, namely aldehydes and ketones, are not only found in large numbers in widely distributed natural products, but are also used industrially to a considerable extent both as reactants and as solvents in organic synthesis. The carbonyl group is one of the most important functional groups in organic chemistry.

A large number of methods for preparing carbonyl compounds have been described in the prior art. Alcohols are generally used as reactants, which are advantageous with respect to the sustainability of carbonyl preparation since they are present in large amounts in nature in the form of carbohydrates (sugar, saccharides, starches, glycosides, glycosyls) and can be readily converted into other alcohol derivatives (e.g. anhydrosugars, sugar alcohols and the like) by methods already established.

The methods described in the prior art for oxidizing alcohols to carbonyl compounds are associated with disadvantages which oppose their use on an industrial scale.

Sheldon et al. (Sheldon, Roger A.; Arends, Isabel W. C. E. Journal of Molecular Catalysis A: Chemical (2006), 251(1-2), 200-214.) and Minisci et al. (Minisci, Francesco; Punta, Carlo; Recupero, Francesco. Journal of Molecular Catalysis A: Chemical (2006), 251(1-2), 129-149.) thus describe a method for oxidizing alcohols with oxygen using nitroxyl radical derivatives and with addition of transition metals, which requires that the said transition metals have to be removed in the form of salts after the synthesis in a complex manner. Moreover, these salts are toxic.

Other methods use expensive oxygen sources, e.g. hypochlorite, chloroperbenzoic acid, peroxomonosulphuric acid, periodic acid or trichloroisocyanuric acid (e.g. L. Anelli, C. Biffi, F. Montanari, S. Quici, *J. Org. Chem.* 52 (1987) 2559; J. A. Cella, J. A. Kelley, E. F. Kenehan, *J. Org. Chem.* 40 (1975) 1850; S. D. Rychovsky, R. Vaidyanathan, *J. Org. Chem.* 64 (1999) 310.; Bolm, Carsten; Magnus, Angelika S.; Hildebrand, Jens P. *Organic Letters* (2000), 2(8), 1173-1175.; S. S. Kim, K. Nehru, *Synletter* (2002) 616.; De Luca, Lidia; Giacomelli, Giampaolo; Porcheddu, Andrea. *Organic Letters* (2001), 3(19), 3041-3043.). Moreover, many of the listed reagents contain halogens, particularly chlorine, bromine and iodine, which can be strongly corrosive under the reaction conditions and often lead to undesired side reactions which reduce the yield. Common disadvantages of the cited oxidizing agents and additives is that they lead to an increased complexity in terms of separation in order to obtain the desired product since they have to be separated optionally in multiple different process steps from the target product.

In a range of methods described in the prior art for oxidizing alcohols to carbonyl compounds, a TEMPO (2,2,6,6-tetramethylpiperidin-1-oxyl) derivative is used as single catalyst or as co-catalyst. Chinnusamy et al. (T. Chinnusamy, O. Reiser, *Chem. Sus. Chem.* 2010, 3, 1040-1042) thus describe the oxidation of benzyl alcohols with oxygen in the presence of a solid TEMPO catalyst and in a carboxylic acid as solvent. A disadvantage of the method described is that significant amounts of cobalt and manganese salts are again used which have to be separated from the target product by removing the solid TEMPO derivative in an additional step. The TEMPO derivative itself has to be prepared, moreover, in a complex and cost-intensive manner beforehand.

Many authors have described the use of immobilized TEMPO derivatives for catalysing the oxidation of alcohols ((a) A. Michaud, G. Gingras, M. Morin, F. Béland, R. Ciriminna, D. Avnir, M. Pagliaro, *Org. Proc. Res. Dev.* 2007, 11, 766-768; (b) A. Michaud, V. Pandarus, L. Tremblay, R. Ciriminna, M. Pagliaro, F. Béland, *Top. Catal.,* 2010, 53, 1110-1113; (c) M. Subhani, M. Beigi, P. Eilbracht, *Adv. Synth. Catal.* 2008, 350, 2903-290 and (d) C: Roben, A. Studer, W. Hemme, H. Eckert, *Synlett* 2010, 1110-1114). The advantage of an immobilized catalyst is that it can be readily separated from a liquid reaction mixture. However, the immobilization is an additional complex process step in addition to the preparation of the catalyst which is generally associated with losses of the corresponding compound.

Against this background, the object of the present invention consists in developing a method for oxidizing alcohols to carbonyl compounds using a catalyst that does not require the use of toxic salts or salts that are difficult to remove or the immobilization of the catalyst. A further object of the present invention consists in developing methods for oxidizing alcohols to carbonyl compounds using a catalyst in which the ratio of product yield to amount of catalyst used is improved compared to the ratios achieved by their use in the methods described in the prior art.

The object is achieved, according to the invention, by the subject matter of the accompanying dependent claims. Preferred embodiments are derived from the dependent claims.

The object is achieved according to the invention in a first aspect by a method for oxidizing a primary or secondary alcohol, preferably to an aldehyde or ketone, comprising the following steps:
   a) providing a catalyst composition comprising at least one nitroxyl radical-containing compound, at least one NO source, at least one carboxylic or mineral acid or an anhydride of a carboxylic or mineral acid,
   b) preparing a reaction mixture by adding at least one primary or secondary alcohol and a gas comprising oxygen, and also optionally comprising one or more solvents, to the catalyst composition from step a) and step e),
   c) incubating the reaction mixture from step b) at a temperature between 0 and 100° C. or at the boiling point of the solvent,
   d) crystallizing the reaction product at the same time as or after step c), and
   e) recovering the catalyst composition by removing the crystallized reaction product from the reaction mixture obtained in step d).

In a first embodiment of the first aspect, the steps b) to e) are repeated at least once, preferably at least three times, and with each repetition of step b) the catalyst composition from step e) is used.

In a second embodiment of the first aspect, which is also an embodiment of the first embodiment, the primary or the secondary alcohol is an aliphatic, cycloaliphatic or aromatic alcohol.

In a third embodiment of the first aspect, which is also an embodiment of the first and second embodiment, the alcohol is a polyhydric alcohol.

In a fourth embodiment of the first aspect, which is also an embodiment of the first and second embodiment, the alcohol is selected from the group comprising aliphatic and linear ω-hydroxycarboxylic acids, sugar alcohols, preferably bicyclic sugar alcohols, and polyols.

In a fifth embodiment of the first aspect, which is also an embodiment of the third embodiment, the alcohol is selected from the group comprising 1,4:3,6-dianhydro-D-mannitol (isomannitol), 1,4:3,6-dianhydro-D-glucitol (isosorbitol) and 1,4:3,6-dianhydro-D-iditol and is preferably 1,4:3,6-dianhydro-D-glucitol (isosorbitol).

In a sixth embodiment of the first aspect, which is also an embodiment of the first to fourth embodiment, the compound containing at least one nitroxyl radical is a compound of the formula I or II,

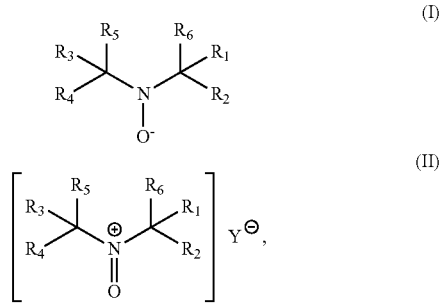

where $R_1$, $R_2$, $R_3$, $R_4$, $R_5$ and $R_6$ are each independently selected from the group comprising (C1-C10)-alkyl, (C1-C10)-alkenyl, (C1-C10)-alkoxy, (C6-C18)-aryl, (C7-C19)-aralkyl, (C6-C18)-aryl-(C1-C8)-alkyl and (C3-C18)-heteroaryl, where the substituents of the type $R_1$, $R_2$, $R_3$, $R_4$, $R_5$ and $R_6$ are identical or different and the substituents of the type $R_5$ and $R_6$ can together form a (C1-C4)-alkylene bridge, which may be saturated or unsaturated, unsubstituted or substituted, particularly having one or more substituents selected from the group comprising $R_1$, C1-C8-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups, and where $Y^-$ is any halogen-free anion.

In a seventh embodiment of the first aspect, which is also an embodiment of the sixth embodiment, the compound containing at least one nitroxyl radical is 2,2,6,6-tetramethylpiperidin-1-oxyl (TEMPO) and/or the derivatives of 2,2,6,6-tetramethylpiperidin-1-oxyl substituted at position 4 of the heterocycle, wherein the derivatives have one or more substituents selected from the group comprising $R_7$, $C_1$-$C_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups, and where $R_7$ is selected from the group comprising $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl and $(C_3-C_{18})$-heteroaryl groups.

In an eighth embodiment of the first aspect, which is also an embodiment of the first to sixth embodiment, the NO source is selected from the group comprising oxygen acids of nitrogen and also salts thereof, preferably nitric acid and nitrous acid, and nitrogen oxide-containing gases.

In a ninth embodiment of the first aspect, which is also an embodiment of the first to seventh embodiment, the mineral acid or the anhydride thereof is selected from the group comprising $H_2CO_3$, $H_3PO_4$, $HNO_3$, $HNO_2$, $H_2SO_4$, $H_2SO_3$, $H_3BO_3$ or anhydrides thereof.

In a tenth embodiment of the first aspect, which is also an embodiment of the first to ninth embodiment, steps c) and d) are carried out separately.

In an eleventh embodiment of the first aspect, which is also an embodiment of the first to ninth embodiment, steps c) and d) are carried out simultaneously.

In a twelfth embodiment of the first aspect, which is also an embodiment of the first to eleventh embodiment, step c) is carried out at a temperature below 70° C.

In a thirteenth embodiment of the first aspect, which is also an embodiment of the twelfth embodiment, step c) is carried out at a temperature below 50° C., preferably below 45° C., more preferably below 35° C.

In a fourteenth embodiment of the first aspect, which is also an embodiment of the thirteenth embodiment, step c) is conducted at a temperature of 0 to 100, preferably 0 to 70; 10 to 50; 10 to 45; more preferably 10 to 45; 15 to 40° C., 20 to 40° C., most preferably at 20 to 35° C.

The basis of the present invention is the surprising finding that it is possible to recover in largely active form and to re-use a catalyst composition comprising a nitroxyl radical-containing compound, a TEMPO catalyst for example, after completion of the reaction by the removal of the reaction product by means of crystallization from the reaction mixture.

A reaction solution is prepared in process step b) which contains all the components which are necessary for the course of the reaction. The catalyst composition used here is either a freshly prepared catalyst composition from step a) or one such from step e) which has already catalysed at least one reaction cycle in the form of step c). Moreover, in a preferred embodiment, at least one reactant is added. In a preferred embodiment, the term "reactant", as used here, includes in this context every component necessary for the reaction which is different from the components of the catalyst composition, preferably the nitroxyl radical-containing compound. In a particularly preferred embodiment, a portion of the initially added catalyst can also be substituted when still catalytically active catalyst composition is present, such as from step e), with the aim of providing a higher yield.

In a preferred embodiment of the present invention, the term "nitroxyl radical-containing compound", as used here, is understood to mean a compound comprising the atom grouping

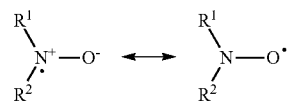

The corresponding nitroxyl radicals do not have a hydrogen atom on the α-carbon atom adjacent to the nitrogen atom. In a preferred embodiment, the terms "nitroxyl radical" and "nitroxyl radical-containing compound", as used here, and the like are used synonymously and interchangeably and refer to a compound containing at least one nitroxyl radical.

The nitroxyl radicals used in the catalyst composition in the method according to the invention are preferably compounds according to the structure (I) and/or salts of compounds according to the structure (II):

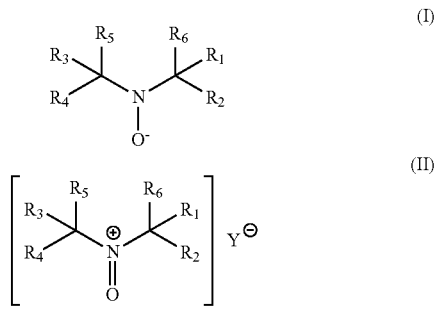

where the substituents $R_1$, $R_2$, $R_3$, $R_4$, $R_5$ and $R_6$ are selected independently from the group comprising (C$_1$-C$_{10}$)-alkyl, (C1-C10)-alkenyl, (C1-C10)-alkoxy, (C6-C18)-aryl, (C7-C19)-aralkyl, (C6-C18)-aryl-(C1-C8)-alkyl and (C3-C18)-heteroaryl groups, where the substituents of the type $R_1$, $R_2$, $R_3$, $R_4$, $R_5$ and $R_6$ are identical or different and the substituents of the type $R_5$ and $R_6$ can together form a (C1-C4)-alkylene bridge, which may be saturated or unsaturated, unsubstituted or substituted, particularly having one or more substituents selected from $R_1$, C1-C8-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups. In the structure (II), Y$^-$ is any halogen-free anion.

It is possible to use more than one nitroxyl radical-containing compound.

In a preferred embodiment, the nitroxyl radicals used in the method according to the invention are 2,2,6,6-tetramethylpiperidin-1-oxyl (TEMPO) and/or derivatives of 2,2,6,6-tetramethylpiperidin-1-oxyl substituted at position 4 of the heterocycle, where the derivatives have one or more substituents selected from $R_1$, C$_1$-C$_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups, where $R_1$ is a (C$_1$-C$_{10}$)-alkyl, (C$_1$-C$_{10}$)-alkenyl, (C$_1$-C$_{10}$)-alkoxy, (C$_6$-C$_{18}$)-aryl, (C$_7$-C$_{19}$)-aralkyl, (C$_6$-C$_{18}$)-aryl-(C$_1$-C$_8$)-alkyl or (C$_3$-C$_{18}$)-heteroaryl group. Examples of appropriate compounds are 4-methoxy-2,2,6,6-tetramethylpiperidin-1-oxyl (4-MeO-TEMPO), 4-oxo-2,2,6,6-tetramethylpiperidin-1-oxyl (4-oxo-TEMPO), 4-hydroxy-2,2,6,6-tetramethylpiperidin-1-oxyl (4-hydroxy-TEMPO), 4-benzoyloxy-2,2,6,6-tetramethylpiperidin-1-oxyl (BnO-TEMPO), 4-acetamido-2,2,6,6-tetramethylpiperidin-1-oxyl, 4-acetamino-2,2,6,6-tetramethylpiperidin-1-oxyl (AA-TEMPO), 4-amino-2,2,6,6-tetramethylpiperidin-1-oxyl, N,N-dimethylamino-2,2,6,6-tetramethylpiperidin-1-oxyl (NNDMA-TEMPO), 3,6-dihydro-2,2,6,6-tetramethyl-1(2H)-pyridinyl oxyl (DH-TEMPO) or bis(2,2,6,6-tetramethylpiperidin-1-oxyl-4-yl) sebacate, where said examples may have one or more substituents selected from $R_1$, C$_1$-C$_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino groups.

In a preferred embodiment, the AA-TEMPO, 4-hydroxy-TEMPO, TEMPO and 4-oxo-TEMPO compounds mentioned above are used as nitroxyl radicals in the method according to the invention. In a more preferred embodiment of the present invention, AA-TEMPO, 4-hydroxy-TEMPO and TEMPO, particularly AA-TEMPO, are used.

In a preferred embodiment, the proportion of nitroxyl radical is, with increasing preference, 0.001 to 10 mol %, 0.01 to 5 mol % or 0.1 to 2 mol %, based on the amount of alcohol used.

The method may be used for oxidizing primary and secondary alcohols. Particularly preferred is a sugar alcohol, which, in a preferred embodiment, as used here, is understood to mean a carbohydrate having at least one hydroxyl group. In a particularly preferred embodiment, this refers to a bicyclic sugar alcohol. In a preferred embodiment, "bicyclic sugar alcohol", as understood here, is understood to mean a sugar alcohol which may form, at least transiently, two ring systems. In a very particularly preferred embodiment, a sugar alcohol is a dianhydrohexitol or a compound from the group comprising 1,4:3,6-dianhydro-D-mannitol, 1,4:3,6-dianhydro-D-glucitol (isosorbide) and 1,4:3,6-dianhydro-L-iditol.

In addition, the catalyst composition used in the method according to the invention comprises at least one NO source. In a preferred embodiment of the present invention, ammonium nitrate or ammonium nitrite may be used as the NO source. In a more preferred embodiment, nitrogen oxide-containing gases such as $N_2O$, NO, $N_2O_3$, $NO_2$, $N_2O_4$, and $N_2O_5$ may be used as the NO source. In a still more preferred embodiment, oxygen acids of nitrogen are used as NO source, particularly nitric acid or nitrous acid. Mixtures of the different NO sources mentioned above may also be used as the NO source. In a preferred embodiment, the proportion of the NO source(s) used in the method according to the invention is 0.001 to 10 mol %, preferably 0.01 to 5 mol % and especially preferably 0.1 to 2 mol %, based on the amount of alcohol used. In a particularly preferred embodiment, the NO source is regenerable with oxygen and/or separable under crystallization conditions. In a further particularly preferred embodiment, the NO source has a water content of less than 10, preferably less than 7.5, 5, 2.5, 1.5, 1 or 0.5% (w/v) water.

The oxidizing agent used in the method according to the invention is an oxygen-containing gas. In a preferred embodiment, pure oxygen is used as the oxygen-containing gas but mixtures of oxygen with an inert gas or air or a gas participating in the reaction may also be used. Suitable inert gases are, for example, nitrogen, carbon dioxide, helium or argon. Gases participating in the reaction which can be used are, for example, nitrogen oxides, which have already been mentioned in the description of the NO sources. The partial pressure of oxygen is preferably 0.1 to 100 bar, particularly preferably 0.2 to 50 bar. In a preferred embodiment, the term "oxygen-containing gas", as used here, is understood to mean a gas or gas mixture comprising free molecular oxygen, i.e. $O_2$.

The oxidation reaction may be conducted in the presence or absence of solvent; preferably the reaction is performed in a solvent. In a particularly preferred embodiment of the present invention, the solvent used is a solvent in which the alcohol reactant is more soluble at a given temperature than the carbonyl compound formed therefrom during the oxidation.

Polar solvents are preferably used here, particularly polar organic solvents. The solvents preferably used are acetonitrile, tetrahydrofuran, ethyl acetate, acetone, diethyl ether, methyl tert-butyl ether, tertiary alcohols such as tert-amyl alcohol, tert-butyl alcohol, esters of carbonic acid such as dimethyl carbonate, diethyl carbonate, hydrocarbons, carboxylic acids, carboxylic acid anhydrides or a mixture of these solvents. In a preferred embodiment of the present invention, with increasing preference, 0.1 to 70% by volume, 0.5 to 60% by volume or 1 to 50% by volume of solvent are used, based on the amount of alcohol used. Particularly preferred solvents include, but are not limited to, the group of the carboxylic acids or the anhydrides thereof. The carboxylic acids or carboxylic acid anhydrides which may be used in the method according to the invention are, for example, acetic acid, propionic acid, butyric acid, pentanoic acid, 2-ethylhexanoic acid, anhydrides thereof or another carboxylic acid or another anhydride that is soluble in the reaction mixture. In a particularly preferred embodiment, in the method according to the invention, one solvent is used selected from the group comprising acetic acid, pentanoic acid and 2-ethylhexanoic acid. It is also possible to use mixtures of different suitable carboxylic acids or solutions of carboxylic acids in a suitable solvent. In each case, a solvent should be selected in which the catalyst comprising the nitroxyl radical is sufficiently soluble. Those skilled in the art have the capability to determine and establish the solubility of a substance, such as that of the catalyst in a solvent, by routine experimentation and the amount of substance can be taken up by the solvent such that precipitation of the catalyst or similar undesired effects do not occur.

In a preferred embodiment of the present invention, step c) is carried out at a temperature $T_O$ of 0 to 100° C., or at the boiling point of the solvent. Particularly preferably is 10° C.$<T_O<$80° C. and especially preferably is 15° C.$<T_O<$50° C.

The total pressure for the oxidation in the method according to the invention is preferably 1 to 300 bar, preferably 1 to 50 bar and especially preferably 1 to 5 bar.

The process step c) may be carried out either in batch, semi-batch or in continuous mode. Furthermore, the process step c) is not linked to any particular reactor type, rather the process step may be carried out in a stirred tank, in a tubular reactor, in a tank cascade or a combination of these reactor types. In an embodiment of the present invention, the alcohol is initially dissolved or suspended in a suitable solvent, and the catalyst composition is then added to this solution or suspension separately or as a mixture. The pressure and temperature are then adjusted. It is also possible, however, to charge the catalyst composition and to add the solution or suspension of the alcohol to the catalyst composition. In the case of a continuous process control, the alcohol is preferably fed with the reaction gases into a reactor in the configuration of a trickle bed or bubble column. It is particularly advantageous to the method according to the invention when the water content in the reaction composition is as low as possible, since high proportions of water can reduce the yields. Moreover, the reaction can be accelerated by removing the water of reaction from the reaction in progress.

In order to keep the water content as low as possible, several method variants are provided. In terms of an efficient process control avoiding additional coproducts, the addition of water-removing additives, which work by chemical or physical means, to the reaction mixture, should be avoided. In place of this, nascent water in process step c) may be distilled off continuously from the reaction mixture. A preferred method variant consists in the chemical binding of the water of reaction to the carbonyl compound being generated, wherein this formation of the carbonyl hydrates proceeds spontaneously. Following isolation of the carbonyl hydrates according to the subsequently implemented process step d), these carbonyl hydrates, in an optional process step, may again be separated into water and carbonyl compound. Such a process step may comprise, for example, drying or vacuum sublimation. Although the carbonyl compounds described in this invention are starting products for subsequent syntheses, the carbonyl hydrates may also alternatively be used in unchanged form, i.e. without prior elimination of water. Such subsequent syntheses may comprise, for example, condensation reactions of the carbonyl group, such as reactions with nucleophiles, e.g. ammonia, amines, hydrazines and the like.

The crystallization of the carbonyl compound or the carbonyl hydrate in step d), depending on the solubility of the alcohol and carbonyl compound or carbonyl hydrate and also the reactant concentration used, may take place sequentially after performing the oxidation reaction or also at the same time as the latter in process step c). In the sequential mode, the oxidation and crystallization are preferably conducted in a stepwise manner; however, a continuous mode is also possible if the locations of the reaction and crystallization are spatially separated, e.g. by apparatuses connected in series. The precise conditions under which the carbonyl compounds may be caused to crystallize may be determined by those skilled in the art by way of routine experimentation. Suitable approaches and parameters to be considered are described in the prior art, for example "Organikum—Organisch-chemisches Grundlagen-praktikum", $22^{nd}$ edition, publisher Wiley-VCH.

Step e) of the method according to the invention comprises the recovery of the catalyst composition by removing the crystallized reaction product from the reaction mixture obtained in step d). Suitable methods which can be easily carried out for removing a crystallized reaction product from a liquid reaction solution are known to those skilled in the art. For example, the mixture may be centrifuged or simply be allowed to stand until the insoluble crystals have settled out at the bottom of the vessel, whereupon the aqueous solution is simply decanted off. Alternatively, the solution may be filtered. The removal of the crystallized reaction product may also comprise removing the water to which it is bound. The aforementioned separation procedures may also be carried out continuously.

In the case of sequential crystallization, the crystallization temperature $T_K$ in process step d) may differ from the oxidation temperature $T_O$ in process step c). Here, $T_K$ must be selected such that, under the given concentration conditions, it is neither below the solubility limit of the alcohol reactant optionally still remaining in the reaction mixture nor below the solubility limit of the catalyst system present in the reaction mixture. In a preferred embodiment, the crystallization is conducted by lowering the temperature to at least 10° C. and/or to a temperature between 0 and 25, preferably 0 and 20, more preferably 5 and 18, most preferably 10 to 17.5° C.

In the case of parallel crystallization, $T_K=T_O$, wherein the solubility of the carbonyl compound or the carbonyl hydrate at $T_O$ is thus considerably lower than that of the reactant present in the reaction mixture, such that the carbonyl compound or the carbonyl hydrate precipitates during the oxidation. In this case, a continuous mode is preferred, in which the reaction mixture is continuously fed through a separation apparatus (e.g. a filter press) optionally spatially separated from the reactor and the resulting reaction mixture, depleted of carbonyl compound or carbonyl hydrate, is reintroduced into the reactor.

The parallel crystallization method is preferred in the context of a continuous operating mode for process step c).

In a preferred embodiment, the optionally carbonyl hydrate-containing product obtained from the process step e) described is converted, in an optional process step, to the water-free carbonyl compound by water removal.

The temperature during the reaction in step c) must take account of, on the one hand, an optimal yield and the demand of a rapid reaction course and, on the other hand, the durability and stability of the reagents and products. In a preferred embodiment of the present invention, step c) is conducted at a temperature, with increasing preference, of below 70, 65, 60, 55, 50, 45, 40 or 30° C. In a preferred embodiment, the term "conducted at a temperature below X° C.", as used here, means that the temperature averaged over the time course of step c) is below X° C.

The present invention is further illustrated by means of the following FIGURE and the following example, from which further features, embodiments and advantages arise.

FIG. 1 shows the amounts of reactant, product and intermediates during oxidation of isosorbide in an experiment with 9-fold recycling of the TEMPO catalyst.

EXAMPLE 1

Oxidation of Isosorbide

In a 250 mL four-necked flask heated in a water bath equipped with magnetic stirrer, reflux condenser, internal thermometer and gas inlet tube (with frit), 14.63 g of isosorbide (100 mmol) are dissolved with stirring in 78.94 g of glacial acetic acid. The reaction mixture is then saturated with oxygen over a period of 20 min. Meanwhile, 1.5 g of AA-TEMPO (7 mmol) are dissolved in 25.03 g of glacial acetic acid. After the purging time is complete, this solution is added to the reaction mixture together with 0.47 g of fuming nitric acid (7 mmol) and the reaction thereby initiated. After stirring for 6 h at 25° C., the reaction mixture is cooled to 15° C. and allowed to crystallize for 12 h. Precipitating diketone is thereafter to removed under suction and the resulting mother liquor is again treated with sufficient isosorbide, AA-TEMPO, nitric acid and acetic acid so that the original starting concentrations of the three substances in the original amount of acetic acid is again reached. Following renewed reaction, crystallization occurs as described above and the diketone is removed. The reaction procedure and crystallization is carried out ten times in total; the amounts of isosorbide and catalyst used and the amounts of diketone obtained are summarized in FIG. 1 and Table 1. The data reveal that the AA-TEMPO catalyst can be re-used 3.5 times and the $HNO_3$ catalyst 2.6 times and at the same time the overall yield of diketone reaches a value of 93% (based on isosorbide used).

TABLE 1

Initial weights of isosorbide, AA-TEMPO and nitric acid and resulting weights of diketone in oxidation of isosorbide; 10-fold recycling experiment

| Experiment No. | $m_{isosorbide}$ [g] | $m_{AA\text{-}Tempo}$ [g] | $m_{HNO3}$ [g] | $m_{diketone}$ [g] |
|---|---|---|---|---|
| 1 | 14.64 | 1.50 | 0.47 | 3.77 |
| 2 | 14.00 | — | — | 10.19 |
| 3 | 14.70 | — | — | 9.89 |
| 4 | 14.66 | — | — | 1.12 |
| 5 | 11.17 | 0.70 | — | 0.86 |
| 6 | — | — | 0.47 | 8.56 |
| 7 | 14.17 | 0.30 | — | 44.57 |
| 8 | 14.72 | — | — | 0.00 |
| 9 | 7.77 | 0.75 | 0.24 | 26.66 |
| 10 | 14.77 | — | 0.24 | 0.00 |
| Total [g] | 120.60 | 3.25 | 1.42 | 105.63 |
| Total [mmol] | 825.24 | 16.31 | 22.54 | 743.30 |
| mol % | 100.0 | 2.0 | 2.7 | 92.6 |

The invention claimed is:

1. A method for oxidizing a primary or secondary alcohol, the method comprising:
   a) preparing a catalyst composition having an initial concentration of each of a nitroxyl radical-comprising compound, a NO source, and a carboxylic or mineral acid or an anhydride of a carboxylic or mineral acid;
   b) adding at least one primary or secondary alcohol and a gas comprising oxygen and optionally also one or more solvents to the catalyst composition to obtain a reaction mixture;
   c) incubating the reaction mixture at a temperature between 0 and 100° C. or at a boiling point of the solvent, to obtain an oxidation reaction product of the primary or secondary alcohol in the reaction mixture;
   d) crystallizing the oxidation reaction product in the reaction mixture;
   e) removing the crystallized reaction product from the reaction mixture; and
   f) recovering the catalyst composition by adding the nitroxyl radical-comprising compound, the NO source, and the carboxylic or mineral acid or an anhydride of a carboxylic or mineral acid to the initial concentration;
   g) repeating operations b) through f) with the recovered catalyst composition.

2. The method of claim 1, wherein the primary or secondary alcohol is an aliphatic, cycloaliphatic or aromatic alcohol.

3. The method of claim 1, wherein the primary or secondary alcohol is a polyhydric alcohol.

4. The method of claim 1, wherein the primary or secondary alcohol is selected from the group consisting of an aliphatic acid, a linear ω-hydroxycarboxylic acid, a sugar alcohol, and a polyol.

5. The method of claim 3, wherein the primary or secondary alcohol is selected from the group consisting of 1,4:3,6-dianhydro-D-mannitol, 1,4:3,6-dianhydro-D-glucitol (isosorbitol) and 1,4:3,6-dianhydro-D-iditol.

6. The method of claim 1, wherein the nitroxyl radical-comprising compound is of formula I or II,

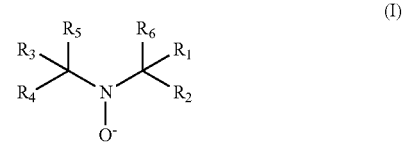

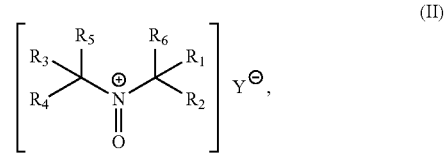

wherein $R_1$, $R_2$, $R_3$, $R_4$, $R_5$ and $R_6$ are each independently selected from the group consisting of (C1-C10)-alkyl, (C1-C10)-alkenyl, (C1-C10)-alkoxy, (C6-C18)-aryl, (C7-C19)-aralkyl, (C6-C18)-aryl-(C1-C8)-alkyl and (C3-C18)-heteroaryl, and $R_5$ and $R_6$ optionally form a (C1-C4)-alkylene bridge, which may be saturated or unsaturated, unsubstituted or substituted, and $Y^-$ is a halogen-free anion.

7. The method of claim 6, wherein the nitroxyl radical-comprising compound is 2,2,6,6-tetramethylpiperidin-1-oxyl (TEMPO), a derivative of 2,2,6,6-tetramethylpiperidin-1-oxyl substituted at position 4 of the heterocycle, or both, wherein the substituent at the 4 position of the derivative of 2,2,6,6-tramethylpiperidin-1-oxyl comprises one or more substituents selected from the group consisting of $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl and $(C_3-C_{18})$-heteroaryl optionally substituted with a substituent selected from the group consisting of $C_1-C_8$-amido, halogen, oxy, hydroxyl, amino, alkylamino, dialkylamino, arylamino, diarylamino, alkylcarbonyloxy, arylcarbonyloxy, alkylcarbonylamino and arylcarbonylamino.

8. The method of claim 1, where the NO source is selected from the group consisting of an oxygen acid of nitrogen, a salt thereof, and a gas comprising nitrogen oxide.

9. The method of claim 1, wherein the catalyst composition comprises a mineral acid or anhydride thereof, selected from the group consisting of $H_2CO_3$, $H_3PO_4$, $HNO_3$, $HNO_2$, $H_2SO_4$, $H_2SO_3$, $H_3BO_3$ and anhydrides thereof.

10. The method of claim 1, wherein c) and d) are performed separately.

11. The method of claim 1, wherein c) and d) are performed simultaneously.

12. The method of claim 1, wherein c) is performed at a temperature below 70° C.

13. The method of claim 1, wherein c) is performed at a temperature below 50° C.

14. The method of claim 1, wherein c) is performed at a temperature of 10 to 50° C.

15. The method of claim 1, comprising preparing a reaction mixture by adding at least one primary alcohol in b).

16. The method of claim 1, comprising preparing a reaction mixture by adding at least one secondary alcohol in b).

17. The method of claim 1, wherein the primary or secondary alcohol is oxidized to an aldehyde or ketone.

18. The method of claim 1, wherein the one or more solvents are present in the reaction mixture.

19. The method of claim 1, wherein the alcohol is a bicyclic sugar alcohol.

* * * * *